United States Patent [19]

Blake-Haskins et al.

[11] Patent Number: 5,723,107
[45] Date of Patent: Mar. 3, 1998

[54] DUAL COMPONENT DENTIFRICE COMPOSITION FOR FLUORIDATING TEETH

[75] Inventors: John C. Blake-Haskins, Piscataway; Mary L. Colligan, Somerville; Benjamin Y. Mandanas, Freehold; Abdul Gaffar, Princeton, all of N.J.

[73] Assignee: Colgate Palmolive Company, New York, N.Y.

[21] Appl. No.: 726,974

[22] Filed: Oct. 7, 1996

Related U.S. Application Data

[60] Provisional application No. 60/006,163 Nov. 2, 1995.
[51] Int. Cl.⁶ .................... A61K 7/16; A61K 7/18
[52] U.S. Cl. ............................... 424/52; 424/49
[58] Field of Search ............................ 424/49–88

[56] References Cited

U.S. PATENT DOCUMENTS

| | | | |
|---|---|---|---|
| 4,048,300 | 9/1977 | Tomlinson et al. | 424/52 |
| 4,080,440 | 3/1978 | DiGiulio | 424/49 |
| 4,083,955 | 4/1978 | Grabenstetter et al. | 424/49 |
| 4,108,980 | 8/1978 | Duff | 424/52 |
| 4,283,385 | 8/1981 | Dhabhar et al. | 424/52 |
| 4,357,318 | 11/1982 | Shah et al. | 424/52 |
| 4,397,837 | 8/1983 | Raaf et al. | 424/52 |
| 4,556,561 | 12/1985 | Brown et al. | 424/151 |
| 5,045,305 | 9/1991 | Clarkson et al. | 424/52 |
| 5,145,668 | 9/1992 | Chow et al. | 424/52 |
| 5,476,647 | 12/1995 | Chow et al. | |
| 5,562,895 | 10/1996 | Tung | 424/57 |
| 5,571,502 | 11/1996 | Winston et al. | 424/52 |
| 5,603,922 | 2/1997 | Winston et al. | 424/49 |
| 5,605,675 | 2/1997 | Usen et al. | 424/49 |
| 5,614,175 | 3/1997 | Winston et al. | 424/52 |

FOREIGN PATENT DOCUMENTS

| | | | |
|---|---|---|---|
| 0089136 | 9/1986 | European Pat. Off. | A61K 7/16 |
| 0263638 | 4/1988 | European Pat. Off. | A61K 7/16 |
| 2170018 | 9/1973 | France | A61K 27/06 |
| 1477823 | 6/1977 | United Kingdom | A61K 7/16 |
| 9507685 | 3/1996 | WIPO | A61K 7/16 |

*Primary Examiner*—Shep K. Rose
*Attorney, Agent, or Firm*—Paul Shapiro

[57] ABSTRACT

A method is disclosed for fluoridating teeth using a two component dentifrice system in which the first component is stable, semi-solid, extrudable dentifrice composition containing a fluoride ion releasable hydrolyzable complex fluoride compound such as sodium fluorosilicate, in an aqueous vehicle in which xanthan gum is the major thickening agent and glycerin, sorbitol or mixtures thereof is the humectant, and the second component is a semi-solid, extrudable dentifrice composition containing a calcium ion releasable compound and an abrasive in an aqueous vehicle containing xanthan gum as the major thickener and glycerin, sorbitol or mixtures thereof as the humectant. The first and second dentifrice compounds are maintained separate from the other until mixed for application to teeth.

14 Claims, No Drawings

DUAL COMPONENT DENTIFRICE COMPOSITION FOR FLUORIDATING TEETH

BACKGROUND OF THE INVENTION

This application claims the benefit of U.S. Provisional Application No. 60/006.163 filing date Nov. 2, 1995.

1. Field of the Invention

This invention is directed to a dentifrice composition containing fluoride compounds effective as anticaries agents and more particularly to a dual component dentifrice composition for fluoridating teeth.

2. The Prior Art

It has long been known to include fluoride containing compounds in dentifrices as anticaries agents, and it has been established that these compounds are effective to reduce the incidence of dental caries. Fluoride compounds which are deemed to be the most effective are sodium fluoride, sodium monoflurophosphate and stannous fluoride. The fluoride compounds are effective mainly due to the fluoride ions which improve the acid resistance of tooth enamel and accelerate recalcification of decayed teeth in their early stage when the decalcification has proceeded only slightly. The effect of improving the acid resistance of the enamel is believed to be due to the fact that the fluoride ions are incorporated into a crystal lattice of hydroxyapatite which is the main constituent of tooth enamel or, in other words, fluoride ions partially fluoridate hydroxyapatite and simultaneously repair the lattice irregularities.

The effectiveness of fluoride treatment in providing acid resistance is dependent upon the amount of fluoride ion which is available for deposition on the enamel being treated. It is, therefore, desirable to formulate dentifrice compositions which provide maximum fluoride ion availability in brushing solutions formed using the dentifrice.

It is known to the art, e.g., U.S. Pat. No. 5,045,305, that an effective way of depositing fluoride on teeth is to use a two-component composition to precipitate calcium fluoride on teeth in which one component contains $CaCl_2$ and the other contains fluoride ions in the form of NaF, the separate components being admixed immediately prior to introduction in the mouth, to effect rapid precipitation of $CaF_2$.

U.S. Pat. No. 5,145,668 discloses a method of fluoridating teeth wherein there is mixed in the mouth a first component comprising a soluble calcium salt such as $CaCl_2$ contained in a non-reactive vehicle and a second component containing a hydrolyzable complex fluoride compound such as sodium fluorosilicate ($Na_2SiF_6$) contained in a non-reactive vehicle, the mixing of the components resulting in hydrolysis of the complex fluoride compound and precipitation of calcium fluoride and its deposition on tooth surfaces. According to U.S. Pat. No. 5,145,668, by the use of the disclosed method, up to 15 times more fluoride (as $CaF_2$) is deposited directly on tooth surfaces from oral formulations compared to previously known formulations containing comparable amounts of fluoride.

Although the method disclosed in U.S. Pat. No. 5,145,668 when practiced using the components in diluted liquid form as a rinse is more efficacious than previously used rinse forms, efforts to practice the method using semi-solid, extrudable non-reactive vehicle formulations such as toothpastes and gels have been unable to provide the theoretical maxima soluble fluoride because of the tendency for the ionic fluoride to be inactivated as the levels of the vehicle ingredients are increased to that required in a semi-solid product such as a toothpaste. Such inactivation renders the fluoride originally included in the toothpaste to be unavailable for interaction with calcium ion to form precipitated $CaF_2$ for fluoride uptake by tooth enamel. The hydrolyzable complex fluorides are believed to interact with ingredients normally considered as inert materials used in the formulation of prior art dentifrice vehicles and that it is such interaction which is believed responsible for the diminished fluoride activity observed when it is attempted to practice the method of U.S. Pat. No. 5,145,668 using semi-solid dentifrices such as toothpaste and gels.

Thus, there is a clear need to formulate a semi-solid dentifrice product utilizing a hydrolyzable complex fluoride compound wherein the ingredients used to prepare the dentifrice vehicle do not interact or otherwise participate in the inactivation of fluoride ion present in the vehicle so that optimum uptake of fluoride is accomplished when the dentifrice is mixed with a calcium ion containing dentifrice and applied to the teeth.

SUMMARY OF THE INVENTION

In accordance with the present invention there is provided a method of fluoridating teeth, the method utilizing two separate semi-solid components which contain ingredients which are reactive when mixed together and applied to the teeth, the first component being a stable, aqueous, semi-solid dentifrice composition containing a fluoride ion releasable, hydrolyzable complex fluoride compound in a vehicle in which the ingredients thereof are non-reactive with the fluoride compound, the vehicle being free of abrasive and surfactant compounds and containing a sufficient amount of a xanthan gum as the major or predominant thickening agent and a humectant comprised of glycerin, sorbitol or mixtures thereof, to impart an extrudable consistency to the composition, the second component having a vehicle containing an abrasive, surfactant and a water soluble calcium ion releasable compound reactive with the fluoride compound and having an extrudable consistency compatible with the first component, whereby maximum fluoride ion availability is provided, as precipitated calcium fluoride, upon mixing of the components and application to teeth.

Dentifrice components containing the fluoride ion releasable hydrolyzable complex fluoride or calcium ion releasable compounds in a vehicle prepared from a specific combination of xanthan gum thickening agent and a glycerin/sorbitol humectant exhibit the desirable rheological characteristics of a semi-solid toothpaste or gel, such characteristics including extrudability, proper viscosity flow rate and ribbon shape retention.

The semi-solid components of the dentifrice composition of the present invention are segregated prior to the point of use and upon being extruded and combined in a ribbon form on the bristles of a toothbrush, remain in a stand-up position on the toothbrush without substantially sinking through the bristles; the combined components complementing one another to provide a convenient and useful composition for increased effective inhibition of caries.

DESCRIPTION OF THE PREFERRED EMBODIMENTS

The first component of the dentifrice composition of the present invention contains a hydrolyzable complex fluoride salt as the source of fluoride. Hydrolyzable complex fluoride salts suitable for use in the practice of the present invention include alkali metal, fluorosilicate, fluorostannate, fluorozirconate, fluoroborate and fluorophosphate salts such as sodium fluorostannate, sodium fluorosilicate, potassium fluorozirconate and potassium fluoroborate. The preferred fluoride compound for purposes of this invention is sodium fluorosilicate ($Na_2SiF_6$).

The hydrolyzable complex fluoride compound is incorporated in the first component of the dentifrice composition of the present invention at a concentration of about 0.1 to about 1% by weight, and preferably at about 0.25 to about 0.5% by weight. At these preferred concentrations, about 750 ppm to about 1500 ppm, fluoride ion will be available to teeth when the combined first and second components of the dentifrice composition are admixed and applied to the teeth.

The vehicle for the hydrolyzable complex fluoride containing component of the dentifrice composition of the present invention is formulated, as further defined hereinunder, to form a semi-solid product of desired consistency which is extrudable from a collapsible tube or pump. In general, the liquids that form the vehicle will comprise chiefly water, in an amount ranging from about 35 to about 60% by weight and preferably about 40 to about 70% by weight and a humectant comprised of glycerin, sorbitol or a mixture of both in an amount greater than about 40% by weight and preferably about 50 to about 65% by weight when used in the preparation of the first component and about 25 to about 60% by weight when used in the preparation of the second component. Commonly employed dentifrice humectants such as low molecular weight polyethylene glycols may not used to prepare the dentifrice composition of the present invention as these glycols has been found to inhibit the activity of the hydrolyzable complex fluoride compound.

It is essential to the practice of the present invention to use xanthan gum as the major or predominant thickening agent for the vehicle used in the formulation of the hydrolyzable complex fluoride containing dentifrice component. Minor amounts of other thickening agents may be tolerated but it is preferred that xanthan be the sole thickening agent.

Xanthan gum is known in the art and has been proposed for use in dentifrice compositions in U.S. Pat. No. 4,401, 648. Xanthan gum is a fermentation product prepared by action of the bacteria of the genus Xanthomonas upon carbohydrates. Four species of Xanthomonas, viz. *X. campetris, S. phaseoli, X. malvocearum* and *X. carotae* are reported in the literature to be the most efficient gum producers. Although the exact structure is not determined, it is generally accepted to be a heteropolysaccharide with a molecular weight of several million and contains D-glucose. D-mannose, and D-glucoronic acid in molar ratio of 2.8:3:2.0. The molecule contains 4.7% acetyl and about 3% pyruvate. The proposed chemical structure configuration can be found in McNeely and Kang, Industrial Gums, ed. R. L. Whistler, Ch. XXI, 2nd Edition, New York, 1973. The procedure for growing, isolating and purifying the xanthan gum is found in Manufacturing Chemist, May 1960, pages 206–208 (including mention at page 208 of potential use of gums therein described for formulating toothpastes).

Xanthan gum is incorporated in the vehicle of the fluoride component of the dentifrice composition of the present invention in an mount of about 1.2 to 4% by weight and preferably about 1.5 to about 3% by weight.

It has been found necessary to use xanthan gum as the predominant thickening agent in combination with a humectant comprised of glycerine, sorbitol or a mixture thereof in the formulation of the hydrolyzable complex fluoride dentifrice component in order to provide a stable, semi-solid, extrudable dentifrice which exhibits minimal loss of fluoride activity. Other known thickening agents commonly used as dentifrice thickening agents such as guar gum, carboxymethyl cellulose and polyoxyethylene-polyoxypropylene glycol block copolymers have been found to be either incompatible with hydrolyzable complex fluoride compounds causing undue loss of availability of active fluoride ion or a cosmetically unacceptable product is produced which lacks the rheological properties required for an extrudable dentifrice or as in the case of guar gum, have a consumer unacceptable taste.

The use of about 1.5 to about 3% xanthan gum in the preparation of the fluoride component of the dentifrice composition of the present invention is sufficient to form a semi-solid, extrudable, shape retaining product which can be squeezed from a tube or displaced from a pump onto a toothbrush and will not fall between the bristles of the brush but rather, will substantially maintain its shape thereon.

It is also critical to the practice of the present invention that the first component be maintained at an acidic pH and preferably at a pH of about 3 to about 5, preferably about 3.5 to 4.5, as the hydrolyzable complex fluoride salts are stable only at an acidic pH. Acetic acid may be employed to adjust the pH of the hydrolyzable complex fluoride containing dentifrice component to acidic levels.

It is further critical to the practice of the present invention that abrasive materials as well as surfactant materials be excluded from the first hydrolyzable fluoride compound containing dentifrice component. As will hereinafter be demonstrated, abrasive materials such as silica react with and absorb the fluoride compound, and by so doing materially inactivate the fluoride ion upon its release from the hydrolyzable fluoride compound.

It is still further critical to the practice of the present invention that surfactants be excluded from the hydrolyzable fluoride containing first component as most surfactants will hydrolyze in the acidic environment of the first component, substantially reducing the operability of the surfactant.

The second component of the dentifrice composition of the present invention, which is maintained physically separate from the first component until mixing before use, contains a water soluble calcium salt as a source of calcium ion. Examples of suitable soluble calcium salts include calcium chloride, calcium acetate, calcium butylate, calcium citrate, calcium lactate, calcium salicylate, and all other non-toxic salts of calcium and inorganic or organic acids which can dissolve in an aqueous solution to the level required for interaction with the hydrolyzable fluoride compound.

The calcium ion releasable salt is incorporated in the second component of the dentifrice composition of the present invention at a concentration of about 0.4% to about 4% by weight and preferably at about 1.0 to about 1.5% by weight. At the preferred concentrations, about 1350 ppm to about 2000 ppm calcium ion (depending upon calcium salt used) will be available to teeth when the combined first and second components of the dentifrice composition are admixed and applied to the teeth.

The soluble calcium ion containing dentifrice component of the two-component system of the present invention may include a buffer to adjust the pH to a substantially neutral pH, e.g., 6.5 to 7.5. Examples of such buffers include acetate salts and succinate salts. It is preferred that the buffer is an acetate salt when the fluoride and calcium ion containing dentifrice components are mixed together for interaction of the fluoride and calcium ions. The buffer aids in promoting the hydrolysis of the fluoride salt to occur at a steady, high rate, thus providing a continuous high level of fluoride ions to interact with the calcium ions to deposit $CaF_2$ during the time the teeth are exposed to the mixed two-component system.

The calcium ion releasable salt is contained in a vehicle formulated to have a composition similar to the vehicle of the first dentifrice component, so that two components will be of similar physical characteristics, which will permit them to be coextrudable and allow the creation of a desirably attractive striped appearance when the components are of different colors and are extruded together from a toothpaste or pump container. The calcium ion containing second component may optionally contain amounts of other ingredients which are not includable in the first component as, for example, a water insoluble polishing agent or abrasive such as a silica abrasive which is incompatible with the hydrolyzable complex fluoride salt when included in the composition of the fluoride containing first component and has been found to materially reduce the activity of fluoride ion.

It is believed that the adverse effect of abrasives such as silica observed on fluoride activity, when present in the fluoride containing first dentifrice component in combination with hydrolyzable complex fluoride salts such as the fluorosilicate salts, is that abrasives such as silica have very large surface areas which tend to act as a sink for calcium fluoride deposition. Also, fluoride ion may be lost to silica abrasives through chemisorption at the acidic pH at which the first dentifrice component is maintained.

Abrasives which may be included in the second calcium containing component include conventional dentifrice polishing agents, such as silica, calcium carbonate and dicalcium phosphate (anhydrous and/or dihydrate).

Generally, the inclusion of abrasives in dentifrice formulations is necessary for effective cleaning of teeth by brushing. It has been determined that by including an abrasive such as silica in the composition of the second calcium ion containing component of the dentifrice of the present invention, minimal inactivation of fluoride ion occurs when the second component is mixed with the first fluoride ion containing component and the two components are mixed and promptly applied to the teeth.

In order to maintain the physical characteristics of the second component similar to the first component when abrasives are included in the second component of the dentifrice composition of the present invention, the vehicle composition of the second component, specifically the humectant content, is adjusted to accommodate the inclusion of the abrasive. An abrasive is generally included in the second component at a concentration of about 10 to about 30% by weight and preferably at a concentration of about 15 to about 25% by weight. At these abrasive levels, the humectant concentration ranges from about 15 to about 35% by weight and preferably about 20 to about 30% by weight. In such abrasive containing second component, as the inclusion of the abrasive has a thickening effect, the concentration of the xanthan gelling agent is typically lower than in the first component, namely, about 0.75 to about 2% by weight xanthan, and preferably about 1.0 to about 1.75% by weight.

In addition to abrasive materials such as silica being incompatible with hydrolyzable complex fluoride salts, it has been further determined that surfactant compounds, normally included in dentifrice compositions to aid in prophylactic action and to improve detersive and foaming properties, have also been determined to inactivate fluoride ion derived from the hydrolyzable complex fluoride compounds used in the practice of the present invention and therefore, surfactant compounds must be excluded from the composition of the first dentifrice component of the present invention to avoid a diminution of fluoride activity.

Although surfactants are to be excluded from the composition of the first dentifrice component, the surfactant may be usefully incorporated in the second calcium ion containing dentifrice component without materially effecting fluoride ion activity when the components are mixed for use.

Surfactants which may be included in the composition of the second dentifrice component of the present invention include the water soluble salts of the higher alkyl sulfates or sulfoacetate, such as sodium lauryl sulfate, sodium lauryl sulfoacetate or other suitable alkyl sulfate or sulfoacetate having 8 to 18 carbon atoms in the alkyl group; water soluble salts of sulfonated monoglycerides of higher fatty acids, such as sodium coconut monoglyceride sulfonate or other suitable sulfonated monoglyceride of a fatty acid of 10 to 18 carbon atoms; salts of amides of higher fatty acid, e.g., 12 to 16 carbon atom acids, with lower aliphatic amino acids, e.g., taurine or sarcosine, or other amino acid of 2 to 6 carbon atoms, such as sodium-N-methyl-N-palmitoyl tauride, sodium N-lauroyl-, N-myristoyl- and N-palmitoyl sarcosinates; water soluble salts of the esters of such fatty acids with isethionic acid or with glycerol monosulfate, such as the sodium salt of monosulfated monoglyceride of hydrogenated coconut oil fatty acids;water soluble salts of olefin sulfonates, e.g., alkene sulfonates or hydrxoyalkene sulfonates or mixtures thereof having 12 to 16 carbon atoms in the carbon chain of the molecule; and water soluble soaps of higher fatty acids, such as those of 12 to 18 carbon atoms, e.g., coconut fatty acids.

Surfactants are included in the composition of the second calcium ion containing component of the dentifrice of the present invention at a concentration of about 0.5 to about 3.0% by weight and preferably about 1.5 to about 2.5% weight.

Various other materials may be incorporated into the dentifrice preparations of the present invention such as flavoring agents, sweetening agents and coloring materials such as dyes and pigments which are incorporated in the dentifrice compositions of the present invention in amounts which do not adversely affect the properties and characteristics desired in the dentifrice components.

Any suitable flavoring or sweetening materials may be employed in formulating a flavor for both the first and second components of the dentifrice compositions of the present invention. Examples of suitable flavoring constituents include flavoring oils, for example, oils of spearmint, peppermint, wintergreen, sassafras, clove, sage, as well as methyl salicylate. Suitable sweetening agents include lactose, maltose, sodium cyclamate and saccharine. Suitably, flavor and sweetening agents together comprise from about 0.01 to 5% or more of the composition. Preferably, the amount of flavoring oil is about 1.0 to about 2.5% by weight and the sweetening agent is from 0.1 to 4 or 0.1 to 0.5% by weight (the latter range being for artificial sweeteners, such as saccharine).

Coloring materials are generally commercially available food dye solutions which are inert with respect to the ingredients of the components of the dentifrice composition and are included in the components at a concentration of about 0.05 to about 0.2% by weight. Pigments such as $TiO_2$ are preferably excluded from the first dentifrice component of the present invention, for as in the case of abrasives, the relatively large surface area of the pigment tends to act as a sink for calcium fluoride deposition whereby fluoride activity is adversely effected.

The first dentifrice component of the present invention may be prepared by suitable mixing of the ingredients. For instance, in preparing the first component, xanthan gum is dispersed with water and humectants. The hydrolyzable complex fluoride compound, sweetener, buffering agent, flavor and colorant are then separately added and uniformly dispersed. The dentifrice is then thoroughly deaerated (e.g., in vacuo) and packaged. The addition and mixing of the ingredients is conducted in a low humidity environment and preferably under a vacuum of 20–30 inches and preferably 28–30 inches mercury.

The second dentifrice component is prepared in a manner similar to that of the first component except that abrasive, calcium compound, pigment and buffer are substituted for the fluoride compound and buffering agent used in the preparation of the first dentifrice component.

The following specific Examples illustrate the present invention. The individual dentifrice components were prepared by adding xanthan gum to a pre-mix of liquid (typically water and humectant) at a slightly elevated temperature (e.g., from 35° to 60° C.) with proportioning the ingredients to a creamy or gel consistency. Additional ingredients were then added. The amounts of the various ingredients are by weight unless otherwise indicated. The resultant dentifrice was then deaerated, flavor was introduced and the dentifrice was packed in tubes or other containers provided with means for physical separation of the individual dentifrice components.

EXAMPLE 1

A combined dentifrice composition of the present invention, designated "Composition X", composed of a gel (A) and a paste (B) dentifrice component, was prepared having the following ingredients:

| Ingredients | Dentifrice Component A | Dentifrice Component B | % Total Ingredients in Combined Components |
|---|---|---|---|
| Water | 44.930 | 46.555 | 45.595 |
| Glycerin USP | 25.000 | 15.000 | 20.000 |
| Sorbitol (70%) | 25.000 | 10.000 | 17.500 |
| Silica abrasive | 0.000 | 20.000 | 10.000 |
| Xanthan Gum | 3.000 | 1.500 | 2.250 |
| Sodium acetate | 0.000 | 1.205 | 1.000 |
| Flavor | 1.000 | 1.000 | 1.000 |
| Sodium lauryl sulfate | 0.000 | 2.000 | 1.000 |
| Calcium chloride dihydrate | 0.000 | 1.440 | 0.720 |
| Titanium dioxide | 0.000 | 1.000 | 0.500 |
| Sodium Saccharin | 0.300 | 0.300 | 0.300 |
| Sodium Hexafluorosilicate | 0.370 | 0.000 | 0.185* |
| Acetic Acid | 0.300 | 0.000 | 0.150 |
| Food Color solution (green) | 0.100 | 0.000 | 0.050 |
| Total | 100.00% | 100.00% | 100.00% |

*contains 1100 ppm releasable F$^-$

The effect of components A and B when combined and mixed to form Composition X with regard to fluoride uptake was assessed in vitro on cellulose ester disks. This in vitro assessment is correlatable to in vivo delivery. Eight millimeter diameter cellulose ester disks of the type normally used for ultrafiltration processes having a pore size of 0.2 microns, available from BAS Company, West Lafayette Ind., under part no. MF 5658, were used for the fluoride assessment.

One and a quarter grams (1.25 grams) of the A and B dentifrice components prepared in the manner of Example I were diluted with 3.75 grams water to prepare a 1:3 dentifrice/water slurry of each. Each of the diluted slurries were rapidly mixed and a cellulose ester disk was immediately, i.e., within one minute, submerged in the slurry mixture. The available fluoride ion delivered to the slurry was 275 parts per million (ppm). After standing at room temperature for 4 minutes, the cellulose ester disk was removed from the slurry mixture and rinsed in deionized water. The rinsed disks were treated with perchloric acid to etch the fluoride off the disk. The acid etchent was buffered with TISAB (total ionic strength adjusted buffer), supplied by Orion Research, Cambridge, Mass.

The fluoride concentration in the etchent was determined by direct potentiometry with an Orion fluoride ion electrode (Model No. 9409BN) wherein EMF is converted to ppm fluoride in the etchant by means of a logarithmic equation.

Two separate in vitro studies of the two component calcium/fluorosilicate dentifrice system designated Composition X were conducted.

The fluoride deposition results for Composition X are recorded in Table I below.

For purposes of comparison, the procedure was repeated except the dentifrice assayed for fluoride deposition was a widely used commercially available fluoride ion containing toothpaste purchased at a local drug store. This toothpaste was designated "Composition Y". The toothpaste package bore an ADA seal which indicates that the dentifrice contained 1100 ppm fluoride ion. A 1:3 dentifrice/water slurry was then assayed following the procedure of Example I. The deposited fluoride for comparative composition Y is also recorded in Table I.

For purposes of further comparison, a dentifrice designated "Composition Z" containing 1100 ppm sodium fluoride (NaF) was prepared having the following formula:

| INGREDIENT | % BY WEIGHT |
|---|---|
| Water | 6.00 |
| Glycerin | 12.50 |
| Sorbitol | 38.96 |
| SLS | 1.20 |
| Flavor | 0.69 |
| Silica | 23.50 |
| NaF | 0.24 |

A 1:3 dentifrice/water slurry prepared using Composition Z was then assayed following the procedure of Example I. The fluoride deposit results for this comparative assay are also recorded in Table I.

TABLE I

| Composition | Fluoride Deposited on Cellulose Disk (micrograms/cm$^2$) | |
|---|---|---|
|  | Study 1 | Study 2 |
| X | 14.9 ± 5.2 | 9.47 ± 1.58 |
| Y | 0.41 ± 0.25 | 0.16 ± 0.14 |
| Z | 0.33 ± 0.08 | 0.14 ± 0.06 |

The fluoride deposition data recorded in Table I indicate that the combination of components A and B of the present invention (Composition X) deposit 36 to 67 times more fluoride than comparative one component fluoride toothpastes containing the same amount of fluoride ion (Compositions Y and Z).

EXAMPLE II

The procedure of Example I was repeated to prepare a series of dentifrice formulations having the same composition as dentifrice components A and B of Composition X, except the vehicle contained varying amounts of xanthan gum as the thickening agent. For purposes of comparison, the procedure was repeated except that in preparing dentifrice components A and B, that with respect to component A, either polyethylene glycol 600 was substituted for glycerin and sorbitol as the humectant or carboxymethyl cellulose, Pluronic F127 (Polyoxyethylene-polyoxypropylene block copolymer) or guar gum was substituted for xanthan gum or a silica abrasive was added to the component A formulation and that with respect to component B, PEG 600 (polyethylene glycol molecular weight 600) was used as the humectant, or either PEG 2000 (polyethylene glycol molecular weight 2000), carboxymethyl cellulose (CMC) or guar gum was used as the thickener. The compositions of the comparative dentifrice components are also listed in Tables II and III below.

TABLE IV

COMPONENT A COSMETIC PROPERTIES

| Composition | Cosmetic Properties |
| --- | --- |
| 1 | Semi-solid, Extrudable |
| 2 | Semi-solid, Extrudable |
| 3 | Semi-solid, Extrudable |
| 4 | Semi-solid, Extrudable |
| 5 | Semi-solid, Extrudable* |
| 6 | Semi-solid, Extrudable |
| 7 | Semi-solid, Extrudable |
| 8 | Semi-solid, Extrudable |
| 9 | Weak Gel |
| 10 | Runny |
| 11 | Runny |
| 12 | Runny |
| 13 | Did not gel |
| 14 | Runny, stringy |
| 15 | Gooey, gelatinous |
| 16 | Grainy texture, stringy |
| 17 | Grainy texture, weak gel |

*Flavor unacceptable

TABLE II

Dentifrice Component A Composition Concentration (wt. %)

| | Humectant | | | | Thickener | | | | | |
| --- | --- | --- | --- | --- | --- | --- | --- | --- | --- | --- |
| Composition No. | Glyc. | Sorb. | PEG 600 | PEG 2000 | Xan. | CMC | Plur. F127 | Guar Gum | Surfactant SLS | Abrasive Silica |
| 1 | 25 | 25 | — | — | 3.0 | — | — | — | — | — |
| 2 | 25 | 25 | — | — | 3.0 | — | — | — | 1.2 | — |
| 3 | 25 | 25 | — | — | 1.5 | — | — | 1.5 | — | — |
| 4 | 25 | 25 | — | — | 2.0 | — | — | 1.0 | — | — |
| 5 | 25 | 25 | — | — | 1.0 | — | — | 2.0 | — | — |
| 6 | 21.2 | — | — | — | — | — | 20.0 | — | — | — |
| 7 | — | 60.7 | — | — | — | 0.6 | — | — | 1.2 | 25.6 |
| 8 | 25 | 25 | — | — | 1.5 | — | — | — | — | 26.0 |
| 9 | 25 | 25 | — | — | 1.0 | — | — | — | 1.0 | — |
| 10 | 15 | 15 | — | — | 1.2 | — | — | — | — | — |
| 11 | 20 | 20 | — | — | 2.0 | — | — | — | — | — |
| 12 | 20 | 20 | — | — | 1.0 | — | — | 1.0 | — | — |
| 13 | 25 | 25 | — | — | — | — | — | 3.0 | — | — |
| 14 | — | 60.7 | — | — | — | 0.6 | — | — | 1.2 | — |
| 15 | 15 | 44.5 | — | 2.0 | — | — | — | — | 1.2 | — |
| 16 | — | 60.7 | 3.0 | — | — | 0.6 | — | — | — | — |
| 17 | — | 60.7 | 0.6 | — | — | — | — | — | 1.2 | 25.0 |

TABLE III

Dentifrice Component B Composition Concentration (wt. %)

| | Humectant | | | Thickener | | | | |
| --- | --- | --- | --- | --- | --- | --- | --- | --- |
| Composition No. | Glyc. | Sorb. | PEG 600 | Xan. | CMC | Plur. F127 | Surfactant SLS | Abrasive Silica |
| 18 | 10 | 15 | — | 2.0 | — | — | 2.0 | 20.0 |
| 19 | 10 | 15 | — | 1.5 | — | — | 1.5 | 20.0 |
| 20 | 10 | 15 | — | 1.5 | — | — | 1.0 | 20.0 |
| 21 | 10 | 15 | — | 1.0 | — | — | 1.0 | 25.0 |
| 22 | — | 60.7 | 3.0 | 0 | 0.6 | — | 1.2 | 25.0 |

1. Cosmetic Properties

The cosmetic (rheological) properties of dentifrice components A and B having composition numbers 1–22 are recorded in Tables IV and V.

TABLE V

COMPONENT B COSMETIC PROPERTIES

| Composition | Cosmetic Properties |
|---|---|
| 18 | Semi-solid, Extrudable |
| 19 | Semi-solid, Extrudable |
| 20 | Semi-solid, Extrudable |
| 21 | Runny |
| 22 | Semi-solid, Extrudable |

Referring now to compositions 1–17 of Table IV, containing the ingredients set forth for these compositions in Table II, the results recorded in Table IV indicate that when dentifrice component A contain more than 40% by weight humectant and more than 1.2 % by weight of a thickener, dentifrice component A has acceptable cosmetic properties (Compositions 1–8).

By way of contrast, when dentifrice component A is prepared using less than 1.2% xanthan, a weak gel is formed (Composition 9). When the humectant concentration in dentifrice component A is not greater than about 40% by weight (Composition Nos. 10–12), dentifrice component A has unacceptable cosmetic properties, i.e., the compositions are of a runny consistency and are not extrudable. When xanthan is not the predominant thickener in dentifrice component A, (Compositions 13–17) the composition has unacceptable cosmetic properties.

Referring now to compositions 18–22 of Table V containing the ingredients set forth for these compositions in Table III, the results recorded in Table V show that when dentifrice component B prepared in accordance with the present invention, i.e., contains greater than 1% by weight xanthan, the dentifrice component has an acceptable cosmetic appearance.

By way of contrast, when xanthan is present at levels less than 1.2% by weight, e.g., 1% by weight (Composition No. 21) dentifrice component B exhibited poor cosmetic properties.

2. Activity

In a first series of tests to determine the effect on fluoride activity when individual dentifrice component A compositions which had exhibited acceptable rheological properties (Compositions 1–8 of Table II) were combined with a dentifrice component B, composition 22 of Table III, the dentifrices being diluted with water at a 1:3 weight ratio and used to treat cellulose disks in accordance with the procedure of Example I.

The % activity of the combined compositions are recorded in Table VI below, % activity being the % of fluoride uptake on a cellulose disk measured against a combined two component calcium acetate/Na fluorosilicate aqueous control solution wherein the calcium and fluoride ion concentrations are same as present in the 1:3 diluted dentifrice components A and B, namely 480 ppm calcium ion and 275 ppm fluoride ion.

TABLE VI

% Activity of Dentifrice Component A Compositions combined with Dentifrice Component B Composition 22

| Composition No. | % Activity of Combined A and B Components |
|---|---|
| 1 | 104.22 |
| 2 | 89.16 |
| 3 | 35.94 |
| 4 | 39.84 |
| 5 | 55.46 |
| 6 | 8.29 |
| 7 | 50.4 |
| 8 | 31.3 |

The results recorded in Table VI show that when dentifrice component A prepared in accordance with the present invention (Composition 1) is combined with a calcium ion containing dentifrice component B, excellent fluoride activity (104.22%) is observed.

By way of contrast, when a surfactant (SLS) is present in dentifrice component A (Composition 2) a significant reduction in activity is observed (89.16%).

Further, by way of contrast, when xanthan is not the predominant thickener, dentifrice component A exhibits even less activity, note in this regard, Compositions 3–7 wherein activities of 8.3–55.5% are observed. Reduced activity (31.3%) is also observed when an abrasive, e.g., silica is present in dentifrice component A (Composition 8).

In a second series of tests, the sodium fluorosilicate containing dentifrice component identified as Composition 1 in Table II was diluted with water at a weight ratio of 1:3 and combined individually with each of the calcium chloride containing dentifrice components identified as Compositions 18, 19 and 20 in Table III, also diluted 1:3 with water and the % activity of the combined dentifrice components determined. Diluted Composition 1 contained 275 ppm releasable fluoride ion and Compositions 18, 19 and 20 each contained 480 ppm releasable calcium ion. The % activity of the combined dentifrice components was determined and recorded in Table VII below.

TABLE VII

% Activity of Dentifrice Component B Compositions Combined with Dentifrice Component A Composition 1

| Composition No. | % Activity |
|---|---|
| 18 | 146.4 |
| 19 | 103.80 |
| 20 | 99.41 |

The results recorded in Table VII indicate that the dentifrice compositions of the present invention had activity equal to or greater than combined solutions wherein fluoride and calcium concentrations are 275 ppm releasable fluoride ion, 480 ppm releasable calcium ion.

What is claimed is:

1. A method for fluoridating teeth utilizing a semi-solid, extrudable, two component dentifrice system comprising the steps of (1) preparing as a first component a semi-solid, extrudable dentifrice composition containing a fluoride ion releasable hydrolyzable complex fluoride compound in an aqueous acidic vehicle in which the fluoride compound is stable, the vehicle being free of abrasive and surfactant and containing xanthan gum as the major thickening agent and glycerin, sorbitol or mixtures thereof as the humectant, and as a second component, a semi-solid, extrudable aqueous dentifrice composition containing a calcium ion releasable compound and an abrasive in an aqueous vehicle a containing xanthan gum as the major thickening agent and glycerin, sorbitol or mixtures thereof as the humectant (2) maintaining the first and second dentifrice compounds separate from the other until application to teeth requiring fluoridation and (3) mixing the first and second components together to deposit calcium fluoride therefrom on contact with a tooth surface.

2. The method of claim 1 wherein the hydrolyzable complex fluoride compound is sodium fluorosilicate.

3. The method of claim 1 wherein the calcium compound is calcium chloride.

4. The method of claim 1 wherein the first component contains from about 0.1 to about 1% by weight fluoride ion.

5. The method of claim 1 wherein the second component contains from about 0.4 to about 4% by weight calcium ion.

6. The method of claim 1 wherein an abrasive is incorporated only in the second calcium compound containing component.

7. The method of claim 1 wherein a surfactant is incorporated only in the second calcium compound containing component.

8. The method of claim 1 wherein the pH of the first component is between about 3.0 and about 5.0.

9. The method of claim 1 wherein the second component has a pH between about 6.5 and about 7.5.

10. The method of claim 1 wherein the abrasive is silica.

11. The method of claim 1 wherein the surfactant is sodium lauryl sulfate.

12. The method of claim 1 wherein xanthan is the sole thickening agent in the first component.

13. The method of claim 1 wherein the humectant in the first component is present in an amount greater than about 40% to about 65% by weight and is present in the second component in an amount of about 25% by weight to about 60% by weight.

14. The method of claim 12 wherein xanthan is present in the first and second components in an amount between about 1.2 and about 4% by weight.

* * * * *